United States Patent [19]

Barthelemy

[11] Patent Number: 4,849,490
[45] Date of Patent: Jul. 18, 1989

[54] NOVEL BIS(MALEIMIDE)/POLYSILOXANES
[75] Inventor: Pascal Barthelemy, Lyons, France
[73] Assignee: Rhone-Poulenc Chimie, Courbevoie, France
[21] Appl. No.: 159,911
[22] Filed: Feb. 24, 1988
[30] Foreign Application Priority Data
  Feb. 24, 1987 [FR] France .................. 87 02615
[51] Int. Cl.$^4$ .............................. C08G 77/06
[52] U.S. Cl. ...................... 528/15; 528/26; 528/28; 528/38; 548/406
[58] Field of Search ........... 528/26, 38, 28, 15; 548/406
[56] References Cited
  U.S. PATENT DOCUMENTS
  4,581,461  4/1986  Rossi et al. .................. 548/406
  FOREIGN PATENT DOCUMENTS
  2137644A 10/1984 United Kingdom .

Primary Examiner—Melvyn I. Marquis
Attorney, Agent, or Firm—Burns, Doane, Swecker & Mathis

[57] ABSTRACT

Novel diorganopolysiloxylated bis(maleimides) which are readily converted into improved heat-stable polymers have the following general formula (I):

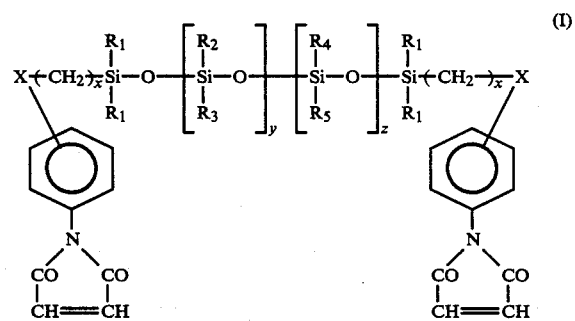

18 Claims, No Drawings

NOVEL BIS(MALEIMIDE)/POLYSILOXANES

CROSS-REFERENCE TO COMPANSION APPLICATIONS

My copending applications, Ser. No. 159,906, and Ser. No. 159,907, both filed concurrently herewith and both assigned to the assignee hereof.

BACKGROUND OF THE INVENTION

1. Field of the Invention

The present invention relates to novel N,N'-disubstituted bis(maleimides) containing a diorganopolysiloxane linkage in their molecular structure, and to a process for preparing such N,N'-bis(maleimides) from maleic anhydride and amines containing a diorganopolysiloxane linkage.

2. Description of the Prior Art

Certain N,N'-disubstituted bis(maleimides) are useful, in particular, for the preparation of heat-stable polyimides. Poly(amide-imides) or linear polyimides containing a diorganopolysiloxane group in their molecular structure, which are manufactured by reacting a tetracarboxylic acid dianhydride or a tricarboxylic acid monoanhydride with, for example, alpha, omegabis-(aminophenoxyalky)diorganopolysiloxanes, are known to this art (see U.S. Pat. Nos. 4,011,279 and 4,395,527). Also known (see British Patent No. 2,137,644) are N,N'-bis(maleimide)siloxanes of the general formula:

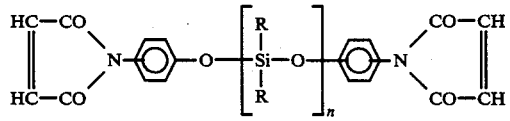

in which R denotes a hydrogen atom, an alkyl radical or a phenyl radical and n is a number ranging from 1 to 6, which are produced by reacting maleic anhydride with alpha, omegabis(aminophenoxy)diorganopolysiloxanes having from 1 to 6

groups; these bis(maleimides) contain in their structure Si—O—C links which, as a result of their poor strength, tend to limit the possible applications thereof.

SUMMARY OF THE INVENTION

Accordingly, a major object of the present invention is the provision of novel N,N'-disubstituted bis(maleimides) containing a diorganopolysiloxane linkage in their molecular structure, but not an Si—O—C bridge, essentially corresponding to the following general formula:

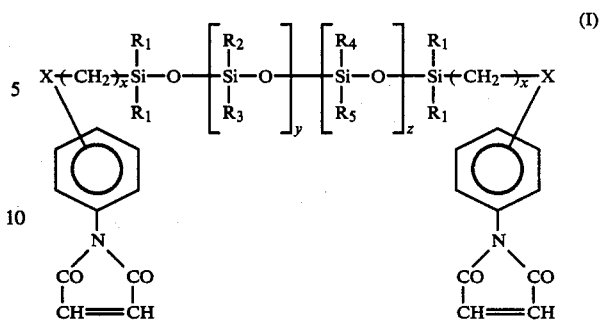

in which:

X, which is in the ortho, meta or para position with respect to the carbon atom of the benzene ring bonded to the nitrogen, denotes one of the following atoms or groups:

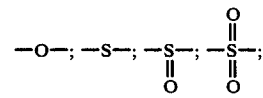

$R_1$, $R_2$, $R_3$, $R_4$ and $R_5$, which may be identical or different, denote monovalent hydrocarbon radical selected from among linear or branched chain alkyl radicals having from 1 to 12 carbon atoms, or substituted such radicals bearing one or more chlorine, bromine or fluorine atom subsituents or a —CN substituent; or a phenyl radical optionally substituted with one or more alkyl and/or alkoxy radicals having from 1 to 4 carbon atoms, or with one or more chlorine atoms;

the symbol x is an integer within the range of from 2 to 8;

the symbols y and z denote numbers, which may be identical or different, integral or fractional, whose sum ranges from 0 to 100.

DETAILED DESCRIPTION OF THE PREFERRED EMBODIMENTS OF THE INVENTION

More particularly according to the present invention, for a compound of the formula (I), when y and/or z are greater than 1, the compound in question is polymeric in structure, and is rarely a single compound, but most often a mixture of compounds having the same chemical structure, which differ in the number of recurring units in their molecule; this gives rise to an average value of y and/or z which may be integral or fractional.

Among the preferred bis(maleimides) according to the present invention, exemplary are those which correspond to the formula (I) in which:

(1) X=—O—; $R_1$, $R_2$, $R_3$, $R_4$ and $R_5$, which may be identical or different, each denote a linear or branched chain alkyl radical having from 1 to 6 carbon atoms; x=2, 3, 4 or 5; and y+z ranges from 0 to 100, and preferably from 4 to 70;

(2) X=—O—; $R_1$, $R_2$ and $R_3$, which may be identical or different, each denote a linear or branched chain alkyl radical having from 1 to 6 carbon atoms; $R_4$ and $R_5$ each denote a phenyl radical; x=2, 3, 4 or 5; and y+z ranges from 0 to 100, and preferably from 4 to 70;

(3) X=—O—; $R_1$, $R_2$ and $R_4$, which may be identical or different, each denote a linear or branched chain alkyl radical having from 1 to 6 carbon atoms; $R_3$ and $R_5$ each denote a phenyl radical; $x=2$, 3, 4 or 5; and $y+z$ ranges from 0 to 100, and preferably from 4 to 70;

(4) $X=-O-$; $R_1$ denotes a linear or branched chain alkyl radical having from 1 to 6 carbon atoms; $R_2$, $R_3$, $R_4$ and $R_5$ each denote a phenyl radical; $x=2$, 3, 4 or 5; and $y+z$ ranges from 0 to 100, and preferably from 4 to 70.

More preferred bis(maleimides) are those which correspond to the formula (I) in which:

(5) $X=-O-$; $R_1=R_2=R_3=R_4=R_5=$linear alkyl radical having from 1 to 3 carbon atoms; $x=2$, 3 or 4; and $y+Z$ ranges from 0 to 100, and preferably from 4 to 70;

(6) $X=-O-$; $R_1=R_2=R_3=$linear alkyl radical having from 1 to 3 carbon atoms; $R_4=R_5=$phenyl radical; $x=2$, 3 or 4; and $y+z$ ranges from 0 to 100, and preferably from 4 to 70;

(7) $X=-O-$; $R_1=R_2=R_4=$linear alkyl radical having from 1 to 3 carbon atoms; $R_3=R_5=$a phenyl radical; $x=2$, 3 or 4; and $y+x$ ranges from 0 to 100, and preferably from 4 to 70;

(8) $X=-O-$; $R_1=$linear alkyl radical having from 1 to 3 carbon atoms; $R_2=R_3=R_4=R_5=$phenyl radical; $x=2$, 3 or 4; and $y+z$ ranges from 0 to 100, and preferably from 4 to 70.

Most preferred bis(maleimides) are those which correspond to the formula (I) in which:

(9) $X=-O-$; $R_1=R_2=R_3=R_5=$methyl radical; $x=3$; and $y+z$ ranges from 0 to 100, and preferably from 4 to 70;

(10) $X=-O-$; $R_1=R_2=R_3=$methyl radical; $R_4=R_5=$phenyl radical; $x=3$; and $y+z$ ranges from 0 to 100, and preferably from 4 to 70;

(11) $X=-O-$; $R_1=R_2=R_4=$methyl radical; $R_3=R_5=$phenyl radical; $x=3$; and $y=z$ ranges from 0 to 100, and preferably from 4 to 70;

(12) $X=-O-$; $R_1=$methyl radical; $R_2=R_3=R_4=R_5=$phenyl radical; $x=3$; and $y+z$ ranges from 0 to 100, and preferably from 4 to 70.

As specific examples of bis(maleimides) which are most especially representative of the present invention, the following are particularly illustrative:

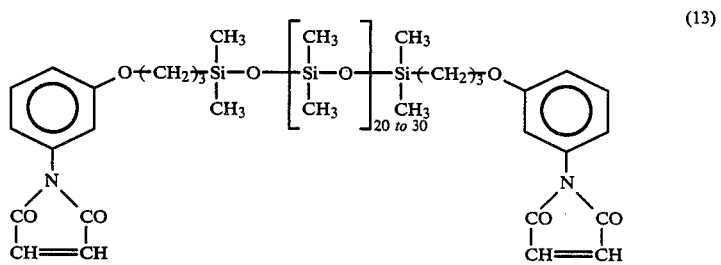

(13)

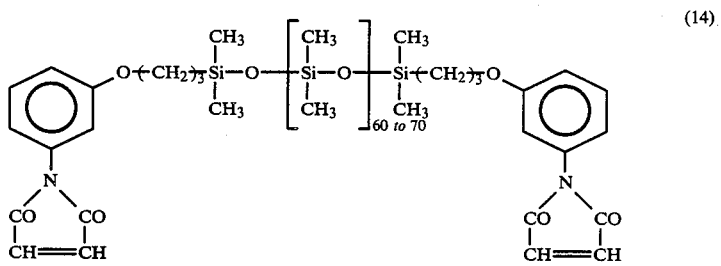

(14)

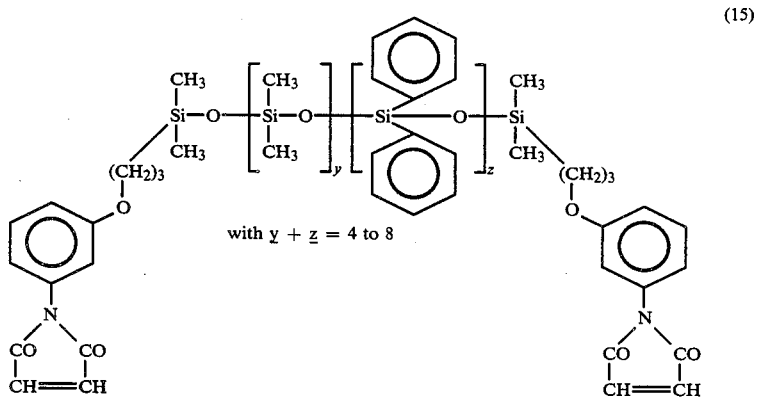

(15)

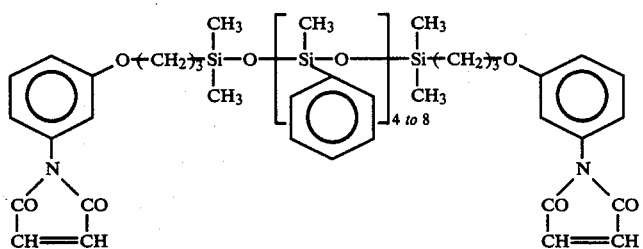
(16)

The present invention also features a process for preparing the bis(maleimides) of formula (I), according to which maleic anhydride is reacted, in the presence of a dehydrating agent, a tertiary amine, an organic diluent and a catalyst, with a diamine containing a diorganopolysiloxane linkage, and having the formula:

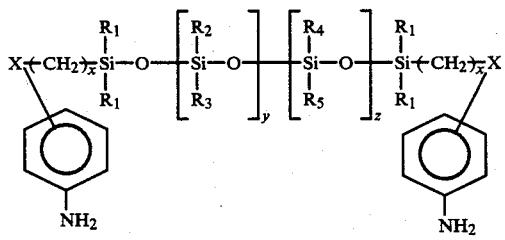
(II)

in which X, $R_1$, $R_2$, $R_3$, $R_4$, $R_5$, x, y and z are as defined above.

These diamines (II) containing a diorganopolysiloxane linkage are compounds which are well known to this art. They are described, for example, in British patent No. 1,062,418 and in U.S. Pat. No. 4,395,527.

According to these patents, a first method for preparing such diamines, which is especially applicable to prepare a compound of formula (II) in which y=z=O, that is to say, when a diamine is prepared containing a diorganodisiloxane group, includes reacting a compound of the formula:

wherein X is as defined above and M is an alkali metal or alkaline earth metal, with a bis(haloalkyl)disiloxane of the formula:

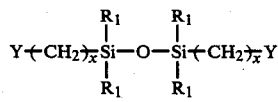

wherein x is as defined above and Y is a chlorine, bromine or iodine atom, at a temperature of from 20° to 200° C., in the presence of an aprotic polar solvent.

In the case where it is desired to prepare a diamine of formula (II) in which y and/or z are other than zero, a second described method of preparation includes copolymerizing one mole of diamine containing a diorganodisiloxane group, prepared as stated above, with a quantity of one or more cyclic diorganopolysiloxanes adapted to provide y moles of siloxy groups of the formula:

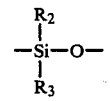

and/or z moles of siloxy groups of the formula:

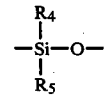

In general, the reaction takes place at a temperature of from 80° to 250° C. in the presence, in this case also, of a solvent and, optionally, of a suitable catalyst.

Another process for preparing the diamines of formula (II), where y and/or z are equal to zero or other than zero, comprises reacting an ethylenically unsaturated compound of the formula:

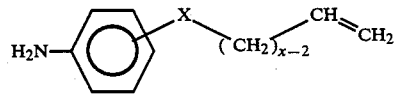

in which X, which is in the ortho, meta or para position with respect to the carbon atom of the benzene ring bonded to the nitrogen, and x are as defined above, with an alpha, omega-bis(hydrogeno)diorganopolysiloxane of the formula:

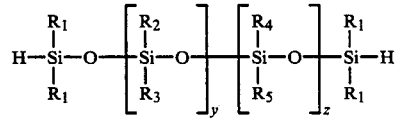

in which $R_1$, $R_2$, $R_3$, $R_4$, $R_5$, y and z are as defined above. This hydrosilylation reaction is carried out in bulk, in the absence of solvent, and using a platinum-based catalyst. The alpha, omega-bis(hydrogeno)diorganopolysiloxanes employed are well known polymers in the silicone art and are, in some instances, commercially available. They are described, for example, in French patents Nos. 2,486,952 and 2,058,988.

When it is decided to employ this hydrosilylation reaction for preparing a diamine of formula (II), the ethylenically unsaturated amino substrate which is well suited for reacting with the alpha, omega-bis(hydrogeno)diorganopolysiloxane is, in particular, an allyloxyaniline of the formula:

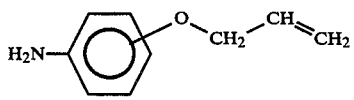

Under these especially favorable conditions, the compounds are hence diamines of formula (II) which will be used to manufacture some of the bis(maleimides) of formula (I), namely, those in which X=—O—, x=3 and $R_1$, $R_2$, $R_3$, $R_4$, $R_5$, y and z are as defined above.

Again considering the process for preparing the bis(maleimides) of formula (I), as stated above, the diamine of formula (II) is reacted with maleic anhydride in the presence of a dehydrating agent, a tertiary amine, an organic diluent and a catalyst.

The maleic anhydride is used in quantities at least equal to one mole per available $NH_2$ group; in general, larger quantities, namely, on the order of 1.01 to 1.5 moles per available $NH_2$ group, are used.

As dehydrating agent, a lower carboxylic acid anhydride, such as acetic anhydride, is advantageously used, in a quantity at least equal to one mole per available $NH_2$ group present in the molecule of diamine of formula (II) introduced. In general, larger quantities, namely, on the order of 1.05 to 1.5 moles per available $NH_2$ group, are used.

Among suitable tertiary amines, trialkylamines and also N,N-dialkylanilines in which the alkyl radicals have from 1 to 12 carbon atoms are particularly representative. Triethylamine and N,N-dimethylaniline are advantageously used. The quantities of tertiary amine generally range from 0.05 to 0.8 mole per available $NH_2$ group.

The reaction is carried out in an organic diluent which is liquid under the working conditions, in practice from 20° to 100° at atmospheric pressure. Among the useful diluents, preferred are those which dissolve the starting maleic anhydride under the temperature conditions adopted for the reaction and in the presence of the other constituents of the reaction mixture.

Among these, the following are particularly representative:

(i) hydrocarbons such as benzene, toluene, cyclohexane;

(ii) chlorinated compounds such as chlorobenzene or methylene chloride;

(iii) cyclic or non-cyclic ethers such as tetrahydrofuran, dioxane or ethyl ether;

(iv) dialkyl ketones such as acetone or methyl ethyl ketone.

As catalysts, it is possible to use a nickel compound which is soluble in the liquid phase of the reaction mixture, such as, for example, nickel salts of carboxylic acids, optionally hydrated, as well as the chelated forms of this metal. The acetate and acetylacetonate are especially suitable. These catalysts are employed in very small quantities, on the order of $0.5 \times 10^{-3}$ to $5 \times 10^{-3}$ moles per mole of available $NH_2$ group.

In practice, for carrying out the process, the first step is to react maleic anhydride with the diamine of formula (II), in the selected diluent at a temperature ranging from 30° to 100° C. for a time ranging, according to the temperature, for a few minutes to 1 hour. The dehydrating agent, the tertiary amine and lastly the catalyst are then added to the reaction medium, and the mixture is then permitted to react under the previously adopted temperature conditions for a time ranging, according to the temperature, from 1 hour to 3 hours. In general, the reaction is terminated by adding a non-solvent such as water, and the bis(maleimide) of formula (I) prepared is then isolated according to the usual methods.

The novel bis(maleimides) of general formula (I) may be used in the form of a mixture with one or more other compounds containing imide groups for preparing heat-stable polymers for molding or for impregnation and which possess desirable mechanical properties.

More specifically, these heat-stable polymers containing imide groups are, in particular, those which comprise the product of reaction, at a temperature ranging from 50° C. to 300° C., between:

(a) an N,N'-bis(maleimide) containing a diorganopolysiloxane group of formula (I);

and (b) an N,N'-bis(maleimide) or a combination of several bis(maleimides) of the formula:

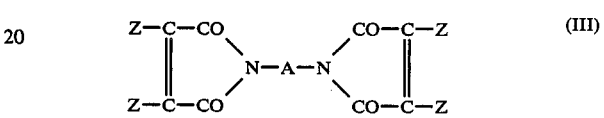

in which:

the symbols Z, which may be identical or different, each denote H, $CH_3$ or Cl; and the symbol A denotes a divalent radical selected from the group consisting of the following radicals: cyclohexylenes; phenylenes; 4-methyl-1,3-phenylene; 2-methyl-1,3-phenylene, 5-methyl-1,3-phenylene; 2,5-diethyl-3-methyl-1,4phenylene; and the radicals of formula:

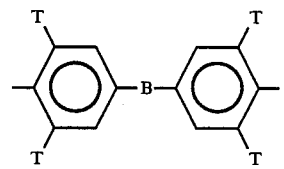

in which B denotes a single valence bond or one of the following groups:

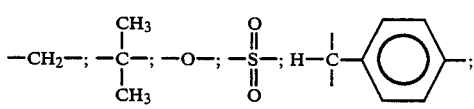

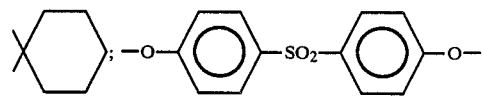

and the symbols T, which may be identical or different, each denote a hydrogen atom or a methyl, ethyl or isopropyl radical.

As regard the bis(maleimides) of formula (I), it is possible to use any one of the compounds of this type which have been described above, when the preparation of the polymers is described, per the text given below, in an organic solvent or diluent.

When the preparation of the polymers is carried out in bulk, the bis(maleimides) of formula (I) preferably used are those in which the diorganopolysiloxane group contains a plurality of Si-phenyl or Si-substituted phenyl bonds. Bis(maleimides) of this type which are suitable are those belonging to the following groups, classified in increasing order of preference:
(a) bis(maleimides) Nos. 2, 3 and 4;
(b) bis(maleimides) Nos. 6, 7 and 8;
(c) bis(maleimides) Nos. 10, 11 and 12.

Among the bis(maleimides) belonging to these preferred groups, those which are most especially suitable are the compounds in which the ratio:

$$\frac{\text{Number of Si—phenyl (optionally substitute) bonds}}{\text{Number of Si—alkyl bonds}}$$

is equal to at least 0.25. By way of specific examples of bis(maleimides) of this type, reference will be made, in particular, to the compounds No. 16.

Exemplary of bis(maleimides) of the formula (III), representative are, in particular:
N,N'-(meta-phenylene)bis(maleimide);
N,N'-(para-phenylene)bis(maleimide);
N,N'-(4,4'-diphenylmethane)bis(maleimide);
N,N'-(4,4'-diphenyl ether)bis(maleimide);
N,N'-(4,4'-diphenyl sulfone)bis(maleimide);
N,N'-(1,4-cyclohexylene)bis(maleimide);
N,N'-[4,4'-(1,1-diphenylcyclohexane)]bis(maleimide);
N,N'-[4,4'-(2,2-diphenylpropane)]bis(maleimide);
N,N'-(4,4'-triphenylmethane)bis(maleimide);
N,N'-(2-methyl-1,3-phenylene)bis(maleimide);
N,N'-(4-methyl-1,3-phenylene)bis(maleimide);
N,N'-(5-methyl-1,3-phenylene)bis(maleimide).

These bis(maleimides) may be prepared according to the processes described in U.S. Pat. No. 3,018,290 and British patent No. 1,137,290. For the preparation of these heat-stable polymers, N,N'-(4,4'-diphenylmethane)bis(maleimide), used either alone or mixed with N,N'-(2-methyl-1,3-phenylene)bis(maleimide), N,N'-(4-methyl-1,3-phenylene)bis(maleimide) and/or N,N'-(5-methyl-1,3-phenylene)bis(maleimide), is preferred.

In the heat-stable polymers described immediately above, the quantities of reactants (a) and (b) are selected such as to have, by weight based on the total weight of these constituents:

(i) from 2 to 50%, and preferably from 5 to 20%, of bis(maleimide) of formula (I); and (ii) from 50 to 98%, and preferably from 80 to 95%, of bis(meleimide)(s) of formula (III).

The above-mentioned polymers containing internal moieties may be prepared by directly heating the reactant (a) and the reactant (b) at least until a homogeneous liquid mixture is obtained. The temperature may vary according to the physical state of the compounds present, but generally ranges from 50° C. to 300° C. It is advantageous to bring the starting compounds to, and maintain them in, a state of intimate mixture before and during the heating, for example using efficient stirring.

The preparation of the polymers may also be accomplished by heating the mixture of reactants in an organic diluent which is liquid over at least part of the range 50° C.–250° C. Among these diluents, representative are, in particular, aromatic hydrocarbons such as xylene and toluene, halogenated hydrocarbons such as chlorobenzenes, polar solvents such as dioxane, tetrahydrofuran and dibutyl ether, dimethylformamide, dimethyl sulfoxide, N-methylpyrrolidone, dimethylacetamide, methyl glycol and methyl ethyl ketone. The solutions or suspensions of polymers may be employed as such for many applications; it is also possible to isolate the polymers, for example by filtration, where appropriate after precipitation by means of an organic diluent which is miscible with the solvent employed. In this context, it is advantageously possible to use a hydrocarbon whose boiling point does not substantially exceed 120° C.

It will be appreciated that the properties of the polymers containing imide groups may vary widely, depending in particular on the exact nature of the reactants introduced, the selected proportions of reactants and the precise conditions of temperature adopted within the range stated above. As regards the polymers produced, the latter may be cured polymers which are insoluble in the usual solvents such as, for example, the compounds mentioned in the preceding paragraph, and which do not display a significant softening below the temperature at which they begin to decompose.

However, these polymers can also be in the form of prepolymers (P) which are soluble in polar organic solvents and possess a softening point at a temperature below 200° C. (in general this softening point ranges from 50° to 150° C.). These prepolymers may be produced in bulk by heating the mixture of reactants until a homogeneous or pasty product is obtained, at a temperature generally from 50° to 180° C., for a period of time which can range from a few minutes to a few hours, this period becoming shorter as the selected temperature is increased. Before the mixture of reactants is subjected to heating, it is advantageous, in this case also, to mix its constituents intimately, beforehand, by stirring. The preparation of the polymers may also be performed in suspension or in solution in a diluent which is liquid over at least part of the range 50°–180° C.

The prepolymers (P) may be used in bulk liquid state, simple hot casting sufficing for shaping and producing molded articles. It is also possible, after cooling and grinding, to use them in the form of powders which are exceptionally suitable for compression molding operations, optionally in the presence of fillers in the state of powders, spheres, granules, fibers or flakes. In the form of suspensions or solutions, the prepolymers (P) may be used for producing coatings and preimpregnated intermediate articles whose reinforcement may consist of fibrous materials based on aluminum silicate or oxide, or zirconium silicate or oxide, carbon, graphite, boron, asbestos or glass. It is also possible to use these prepolymers (P) for producing cellular materials after the incorporation of a blowing agent such as, for example, azodicarbonamide.

In a second stage, the prepolymers (P) may be cured by heating to temperatures on the order of 300° C., generally from 150° to 250° C.; an additional shaping may be carried out during the curing, optionally under vacuum or under a pressure above atmospheric pressure, it also being possible for these operations to be consecutive.

The polymers according to the invention are of value in industrial fields requiring materials endowed with good mechanical and electrical properties as well as great chemical inertness at temperatures of 200° to 300° C. By way of examples, they are suitable for the manufacture of insulators in plate or tubular form for electrical transformers, printed circuit bases, pinions, rings, and the like. The preimpregnated articles are usable for the production of parts having a variety of shapes and functions in many industries such as, for example, in the aeronautical industry. These parts, referred to as laminates, which may be bodies produced by rotation, are obtained by depositing several layers of prepregs on a former or support. The prepregs can also be used as reinforcements or as a means of repairing damaged parts. It is also possible to produce parts by filament winding techniques, with or without a support; it is also possible to carry out injection molding or pultrusion. It will be recalled that, in order to make, for example, molded articles, it is possible to use either the mixture of the reactants or a prepolymer (P) as the starting material. When the mixture of the reactants is used directly as the starting material, this mixture is provided with the shape of the desired article and the curing is then conducted by heating. When the prepolymer (P) is used as the starting material, it may be molded by simple hot casting or by injection, and its curing is then induced by heating.

In order to further illustrate the present invention and the advantages thereof, the following specific examples are given, it being understood that same are intended only as illustrative and in nowise limitative.

EXAMPLE 1

Preparation of the bis(maleimide) of the formula

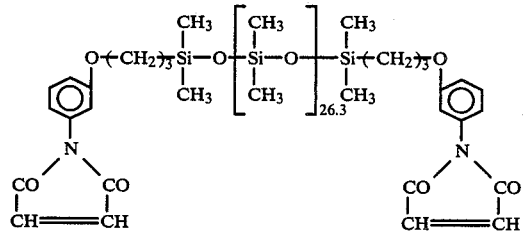

(1.1) Preparation of the diamine containing a diorganopolysloxane group from which the title bis(maleimide) is produced:

A glass reactor equipped with a central stirrer, a dropping funnel and a reflux condenser, in which a slight overpressure of dry nitrogen was establishes, was charged with 45 g (0.0216 mole) of an alpha, omega-bis(hydrogeno)dioragnopolysiloxane of the formula:

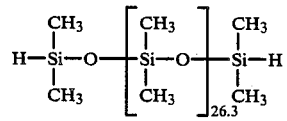

having a molecular weight on the order of 2082 g.

The reactor was then placed in an oil bath preheated to 55° C. and the catalyst was then added. The latter was Karsted's catalyst (complex based on elementary platinum and 1,3-divinyl-1,1,3,3-tetramethyldisiloxane ligands): it was dissolved in toluene (concentration 3.5% by weight) and 120 microliters of this catalyst solution were introduced with a syringe. The ratio r (weight of elementary platinum introduced/weight of the reaction mass) was equal to $60 \times 10^{-6}$.

6.45 g (0.0432 mole) of meta-allyloxyaniline were then permitted to flow gradually into the reactor over a period of 40 minutes, such as to control the exothermic nature of the reaction (the temperature was maintained at 55° C.). One hour after the addition was complete, the mixture was returned back to room temperature.

The product obtained, weighing 51.4 g, was clear brown-orange viscous oil having a proton NMR spectrum in agreement with the structure:

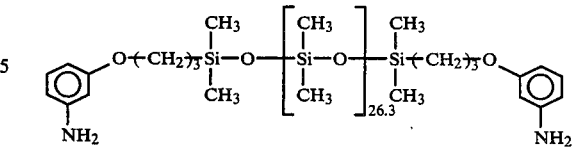

The molecular weight was on the order of 2380 g. Under these conditions, the degree of conversion of the reactants introduced was 100% (neither amine nor hydrogen-containing siloxane oligomer were detected by NMR and infrared analysis) and the yield by weight of desired amine was 100%.

(1.2) Preparation of the bis(maleimide)diorganopolysiloxane:

Using two dropping funnels, the following were introduced simultaneously, over the course of 10 minutes, into a glass reactor equipped with a central stirrer and a reflux condenser, in which a slight overpressure of dry nitrogen was established and which was placed in an oil bath preheated to 55° C.:

(i) 24 cm$^3$ of a solution in acetone of 23.80 g (0.01 mole and 0.02 NH$_2$ groups) of the diaminosiloxane prepared in paragraph (1.1);

(ii) 6 cm$^3$ of a solution of 2.15 g (0.022 mole) of maleic anhydride in acetone.

When the additions were complete, each funnel was rinsed with 5 cm$^3$ of acetone, these portions then being added to the reaction mass maintained under stirring for an additional 15 minutes.

The dropping funnel which contained the maleic anhydride was charged with 2.68 g (0.026 mole) of acetic anhydride, and the other funnel was charged with 0.66 g (0.0006 mole) of triethylamine.

These two compounds were then allowed to flow into the reactor, and 0.1 cm$^3$ of an aqueous solution containing 0.0528 mole of nickel acetate for 100 cm$^3$ of solution was then added.

The reaction mixture was then maintained under reflux under stirring for 2 hours 30 minutes. The temperature was then lowered to 20° C.

The reaction mixture was diluted with 80 cm$^3$ of chilled (5° C.) water with vigorous stirring and the oily product present was then extracted with 80 cm$^3$ of ethyl acetate. The organic phase obtained was washed with three times 80 cm$^3$ of water to attain a value of pH 6 in the washing liquors, and then dried for 2 hours over anhydrous sodium sulfate. After filtration, the ethyl acetate was removed from the organic phase by evaporation, this operation being completed under reduced pressure (approximately 70 Pa) at 60° C., and 24.10 g (equivalent to a yield by weight of 95% with respect to the theoretical value) of a brown-orange viscous product were collected, the NMR spectrum of which was in agreement with the structure of the desired bis(maleimide), which was defined at the beginning of this example. The molecular weight was on the order of 2540 g. In proton NMR (solvent: CDCl$_6$; reference: tetramethylsilane), the absence of the starting diamine was noted and the following chemical shifts, expressed in ppm, were noted:

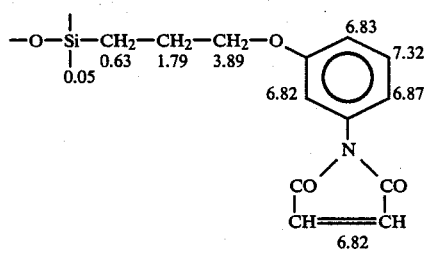

In infrared spectrometry, the pressure of the following bands was noted: $\nu$ (imide C=O)=1710–1730 cm$^{-1}$; $\nu$ (maleimide C—N—C) 1160 cm$^{-1}$; $\nu$ (C—N—C)=1400 cm$^{-1}$.

EXAMPLE 2

Preparation of the bis(maleimide) of the formula

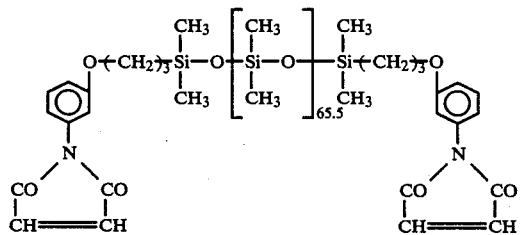

(2.1) Preparation of the diamine containing a diorganopolysiloxane group from which this bis(maleimide) was derived:

The procedure was the same as that described in Example 1, paragraph (1.1), except as regards the following points:

20 g (0.004 mole) of an alpha, omega-bis(hydrogeno)-diorganopolysiloxane of the formula:

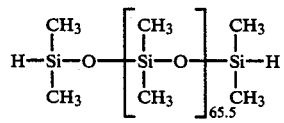

whose molecular weight was on the order of 4982 g, were charged;

50 microliters of the catalyst solution were used; the ratio r (weight of elementary platinum/weight of the reaction mass) was equal to 64×10$^{-6}$; and 1.2 g (0.008 mole) of meta-allyloxyaniline were permitted to flow into the reactor over the course of 45 minutes, and the mixture was returned to room temperature 30 minutes after the addition of this reactant was complete.

The product obtained, weighing 21.1 g, was an orange viscous oil having a proton NMR spectrum in agreement with the structure:

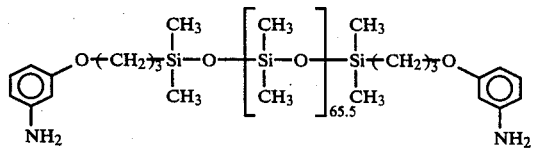

and having a molecular weight on the order of 5280 g. Under these conditions, the degree of conversion of the reactants introduced was 100% (neither amine nor hydrogen-containing siloxane oligomer was detected by NMR and infrared analysis) and the yield by weight of desired diamine was 100%.

(2.2) Preparation of the bis(maleimide)diorganopolysiloxane:

The procedure was the same as that described in Example 1, paragraph (1.2), except as regards the following points:

15 cm$^3$ of a solution in acetone of 21 g (0.004 mole and 0.008 NH$_2$ group) of the diaminosiloxane prepared in paragraph (2.1) above and 3 cm$^3$ of a solution of 0.89 g (0.009 mole) of maleic anhydride in acetone were allowed to flow in;

1.06 g (0.0104 mole) of acetic anhydride and 0.273 g (0.0027 mole) of triethylamine were then allowed to flow in, and 40 microliters of the nickel acetate solution were then added.

20.3 g (equivalent to a yield by weight of 93.5% with respect to the theoretical value) of a brown-orange viscous oil were collected, the NMR spectrum of which was in agreement with the structure of the desired bis(maleimide) which was defined at the beginning of this example. This molecular weight was on the order of 5440 g. In proton NMR, the absence of the starting diamine was noted and the following chemical shifts were noted:

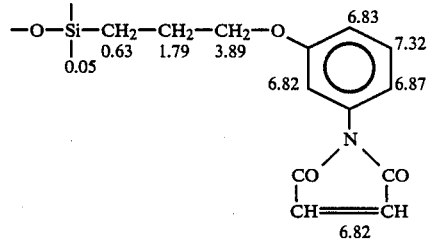

In infrared spectrometry, the presence of the following bands was noted; $\nu$ (imide C=O)=1710–1730 cm$^{-1}$; $\nu$ (maleimide C—N—C)=1160 cm$^{-1}$; $\nu$ (C—N—C)=1400 cm$^{-1}$.

EXAMPLE 3

Preparation of the bis(maleimide of the formula

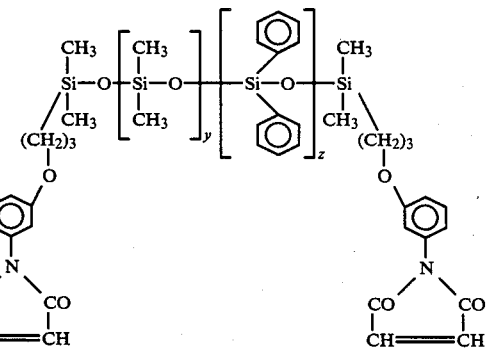

with y + z = 4.99

(3.1) Preparation of the diamine containing a dioraganopolysiloxane group from which this bis(maleimide) was derived:

The procedure was the same as that described in Example 1, paragraph (1.1), except as regards the following points:

105 g (0.07 mole) of an alpha, omegabis(hydrogeno)-diorganopolysiloxane of the formula:

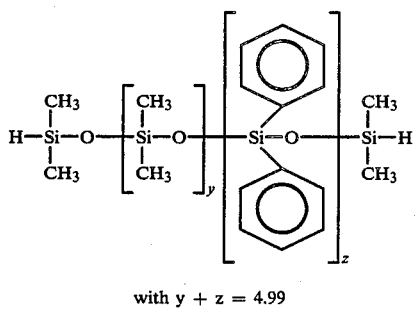

with y + z = 4.99 the molecular weight thereof being on the order of 1492 g, were charged;

350 microliters of the catalyst solution were used; the ratio r (weight of elementary platinum/weight of the reaction mass) was equal to $75 \times 10^{-6}$;

21 g (0.14 mole) of meta-allyloxyaniline were permitted to flow into the reactor over the course of 50 minutes, and the mixture was returned to room temperature 30 minutes after the addition of this reactant was complete.

The product obtained, weighing 125.3 g, was a brown viscous oil having a proton NMR spectrum in agreement with the structure:

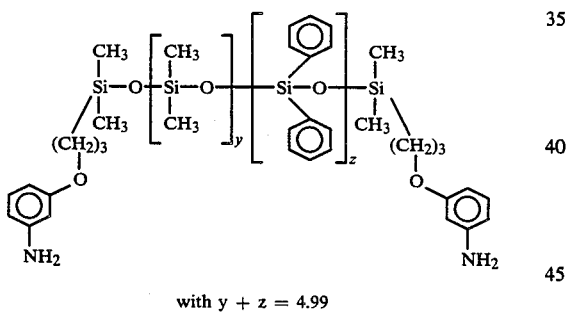

with y + z = 4.99 and having a molecular weight on the order of 1790 g. Under these conditions, the degree of conversion of the reactants introduced was 100% (neither amine nor hydrogen-containing siloxane oligomer was detected by NMR and infrared analysis) and the yield by weight of desired diamine was 100%.

(3.2) Preparation of the bis(maleimide)diorganopolysiloxane:

The procedure was the same as that described in Example 1, paragraph (1.2), except as regards the following points:

50 cm³ of a solution in acetone of 65 g (0.036 mole and 0.072 NH₂ group) of the diaminosiloxane prepared in paragraph 3.1 above and 20 cm³ of a solution of 7.8 g (0.079 mole) of maleic anhydride in acetone were permitted to flow in;

9.6 g (0.094 mole) of acetic anhydride and 2.45 g (0.024 mole) of triethylamine were then allowed to flow in, and 0.5 cm³ of the nickel acetate solution was then added. 69 g (equivalent to a yield by weight of 98% with respect to the theoretical value) of a brown-orange viscous oil were collected, the NMR spectrum of which was in agreement with the structure of the desired bis(maleimide) which was defined at the beginning of this example. Its molecular weight was on the order of 1950 g. In proton NMR, the absence of the starting diamine was noted and the following chemical shifts were noted:

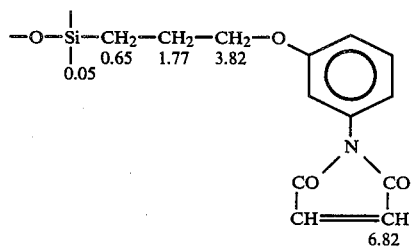

The ratio:

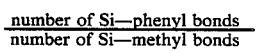

was equal to 0.25.

In infrared spectrometry, the presence of the following bands was noted: $\nu$ (imide C=O)=1710-1730 cm⁻¹; $\nu$ (maleimide-C—N—C)=1160 cm⁻¹; $\nu$ (C—N—C)=1400 cm⁻¹.

EXAMPLE 4

Preparation of the bis(maleimide) of the formula

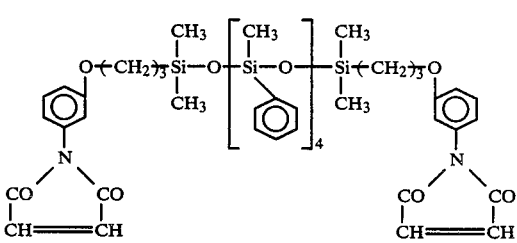

(4.1) Preparation of the diamine containing a diorganopolysiloxane group from which this bis(maleimide) was derived:

The procedure was the same as that described in Example 1, paragraph (1.1), except as regards the following points:

312 g (0.46 mole) of an alpha, omegadis(hydrogeno)-diorganopolysiloxane of the formula:

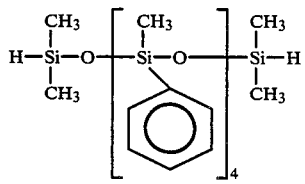

whose molecular weight was on the order of 678 g, were charged;

1.49 cm³ of the catalyst solution were used; the ratio r (weight of elementary platinum/weight of the reaction mass) was equal to $91 \times 10^{-6}$;

137 g (0.92 mole) of meta-allyloxyaniline was permitted to flow into the reactor over the course of 60 minutes, and the mixture was returned to room temperature 30 minutes after the addition of this reactant was complete.

The product obtained, weighing 448.9 g, was a brown-orange viscous oil having a proton NMR spectrum in agreement with the structure:

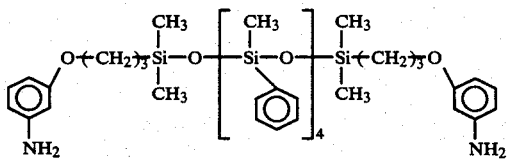

and having a molecular weight on the order of 976 g. Under these conditions, the degree of conversion of the reactants introduced was 100% (neither amine nor hydrogen-containing siloxane oligomer was detected by NMR and infrared analysis) and the yield by weight of desired diamine was 100%.

(4.2) Preparation of the bis(maleimide)diorganopolysiloxane:

The procedure was the same as that described in Example 1, paragraph (1.2), except as regards the following points:

The procedure was the same as that described in Example 1, paragraph (1.2), except as regards the following points:

20 cm$^3$ of a solution in acetone of 25 g (0.025 mole and 0.050 NH$_2$) of the diaminosiloxane prepared in paragraph (4.1) above and 15 cm$^3$ of a solution of 6.4 g (0.055 mole) of maleic anhydride in acetone were allowed to flow in;

6.1 g (0.06 mole) of acetic anhydride and 1.67 g (0.0165 mole) of triethylamine were then allowed to flow in, and 0.3 cm$^3$ of the nickel acetate solution was then added.

27.3 g (equivalent to a yield by weight of 96% with respect to the theoretical value) of a brown-orange viscous oil were collected, the NMR spectrum of which was in agreement with the structure of the desired bis(maleimide) which was defined at the beginning of this example. Its molecular weight was on the order of 1136 g. In proton NMR the absence of the starting diamine was noted and the following chemical shifts were noted:

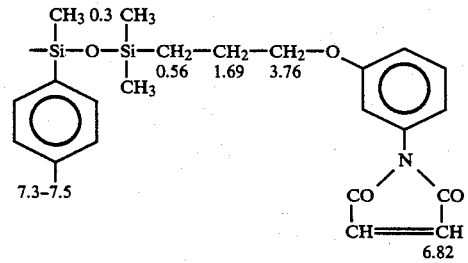

The ratio:

$$\frac{\text{number of Si—phenyl bonds}}{\text{number of Si—methyl bonds}}$$

was determined to be equal to 0.5.

In infrared spectrometry, the presence of the following bands was noted: $\nu$ (imide C=O)=1710–1730 cm$^{-1}$; $\nu$ (maleimide C'N—C)=1160 cm$^{-1}$; $\nu$ (C—N—C)=1400 cm$^{-1}$.

EXAMPLE 5

Preparation of a heat-stable polymer 0.6 g of the bis(maleimide) containing a diorganopolysiloxane group which was described in Example 4 were introduced into a glass reactor equipped with a side tube for degassing and an anchor type stirrer and immersed in an oil bath preheated to 160° C. After 2 minutes of stirring, 70.4 g of N,N'-(4,4'-diphenylmethane)bis(maleimide) were then added over the course of 8 minutes. The mixture was allowed to react further while being stirred for 15 minutes, during the last 5 minutes of which a reduced pressure of 13.3×10$^2$ Pa was applied.

The reaction mass, which was clear in appearance, was then poured into a mold preheated to 150° C. for the purpose of preparing plates having the dimensions 140×100×4 mm, which were subjected to the following curing cycle:

(a) 10 minutes at 160° C.,
(b) 130 minutes at between 160° C. and 250° C.,
(c) 16 hours at 250° C., and
(d) 2 hours at between 250° C. and 25° C.

After release from the mold, the plates based on brown, translucent cured polymer were cut up in order to obtain test pieces having the dimensions 60×10×4 mm, on which CHARPY unnotched impact tests according to NFT Standard 51035 were carried out. The strength at 25° C. thereby obtained was 3.4 kJ/m$^2$.

By way of a comparative test, the operations described above were repeated, charging the reactor, preheated to 175° C., with only 100 g of N,N'-(4,4'-diphenylmethane)bis(maleimide). The mixture was allowed to react under stirring for 12 minutes, during 5 of which a reduced pressure of 6.65 x 10$^2$ Pa was applied.

The cycle of curing the plates molded at 200° C. was as follows:

(i) 1 hour, 45 minutes at 200° C.,
(ii) 1 hour at between 200° and 250° C.,
(iii) 16 hours at 250° C., and
(iv) 2 hours at between 250° C. and 25° C.

The strength at 25° C., measured on the test pieces, was 1.7 kJ/m$^2$.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A diorganopolysiloxylated N,N'-disubstituted bis(maleimide) having the general formula (I):

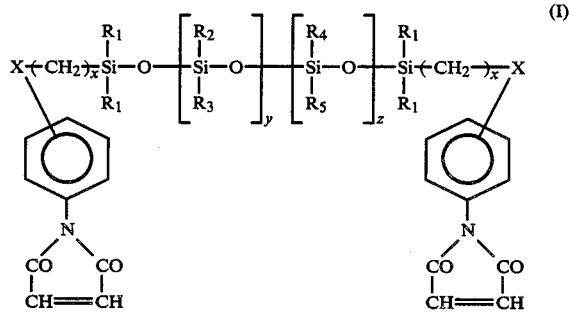

(I)

in which:

X, which is in the ortho, meta or para position with respect to the carbon atom of the benzene ring bonded to the nitrogen, is one of the following atoms or groups:

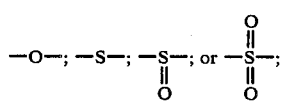

$R_1$, $R_2$, $R_3$, $R_4$ and $R_5$ which may be ientical or different, are each a linear or branched chain alkyl radical having from 1 to 12 carbon atoms, or a substituted such radical bearing one or more chlorine, bromine or fluorine atom substituents or a -CN substituent; or a phenyl radical optionally substituted with one or more alkyl and/or alkoxy radicals having from 1 to 4 carbon atoms, or with one or more chlorine atoms;

the symbol x is an integer ranging from 2 to 8; and the symbols y and z are numbers, which may be identical or different, integral or fractional, the sum of which ranges from 0 to 100.

2. The bis(maleimide) as defined by claim 1, wherein $X=-O-$; $R_1$, $R_2$, $R_3$, $R_4$ and $R_5$, which may be identical or different, are each a linear or branched chain alkyl radical having from 1 to 6 carbon atoms; $x=2, 3, 4$ or 5; and $y+z$ ranges from 0 to 100.

3. The bis(maleimide) as defined by claim 1, wherein $X=-O-$; $R_1$, $R_2$ and $R_3$, which may be identical or different, are each a linear or branched chain alkyl radical having from 1 to 6 carbon atoms; $R_4$ and $R_5$ are each a phenyl radical; $x=2, 3, 4$ or 5; and $y+z$ ranges from 0 to 100.

4. The bis(maleimide) as defined by claim 1, wherein $X=-O-$; $R_1$, $R_2$ and $R_4$, which may be identical or different, are each a linear or branched chain alkyl radical having from 1 to 6 carbon atoms; $R_3$ and $R_5$ are each a phenyl radical; $x=2, 3, 4$ or 5; and $y+z$ ranges from 0 to 100.

5. The bis(maleimide) as defined by claim 1, wherein $X=-O-$; $R_1$ is a linear or branched chain alkyl radical having from 1 to 6 carbon atoms; $R_2$, $R_3$, $R_4$ and $R_5$ are each a phenyl radical; $x=2, 3, 4$ or 5; and $y+z$ ranges from 0 to 100.

6. The bis(maleimide) as defined by claim 1, wherein $X=-O-$; $R_1=R_2=R_3=R_4=R_5=$ linear alkyl radical having from 1 to 3 carbon atoms; $x=2, 3$ or 4; and $y+z$ ranges from 0 to 100.

7. The bis(maleimide) as defined by claim 1, wherein $X=0$; $R_1=R_2=R_3=$ linear alkyl radical having from 1 to 3 carbon atoms; $R_4=R_5=$ phenyl radical; $x=2, 3$ or 4; and $y+z$ ranges from 0 to 100.

8. The bis(maleimide) as defined by claim 1, wherein $X=-O-$; $R_1=R_2=R_4=$ linear alkyl radical having from 1 to 3 carbon atoms; $R_3=R_5=$ a phenyl radical; $x=2, 3$ or 4; and $y+z$ ranges from 0 to 100.

9. The bis(maleimide) as defined by claim 1, wherein $X=-O-$; $R_1=$ linear alkyl radical having from 1 to 3 carbon atoms; $R_2=R_3=R_4=R_5=$ phenyl radical; $x=2, 3$ or 4; and $y+z$ ranges from 0 to 100.

10. The bis(maleimide) as defined by claim 1, wherein $X=-O-$; $R_1=R_2=R_3=R_4=R_5=$ methyl radical; $x=3$; and $y+z$ ranges from 0 to 100.

11. The bis(maleimide) as defined by claim 1, wherein $X=-O-$; $R_1=R_2=R_3=$ methyl radical; $R_4=R_5=$ phenyl radical; $x=3$; and $y+z$ ranges from 0 to 100.

12. The bis(maleimide) as defined by claim 1, wherein $X=-O-$; $R_1=R_2=R_4=$ methyl radical; $R_3=R_5=$ phenyl radical; $x=3$; and $y+z$ ranges from 0 to 100.

13. The bis(maleimide) as defined by claim 1, wherein $X=-O-$; $R_1=$ methyl radical; $R_2=R_3=R_4=R_5=$ phenyl radical; $x=3$; and $y+z$ ranges from 0 to 100.

14. The bis(maleimide) as defined by any of claims 2 to 13, wherein $y+z$ ranges from 4 to 70.

15. A process for the preparation of the bis(maleimide) as defined by claim 1, comprising reacting maleic anhydride, in the presence of a dehydrating agent, a tertiary amine, an organic diluent and a catalyst, with a diamine containing a diorganopolysiloxane linkage and having the formula (II):

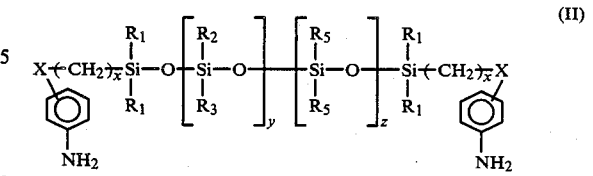

(II)

16. The process as defined by claim 15, wherein the dehydrating agent comprises acetic anhydride.

17. The process as defiend by claim 15, wherein the tertiary amine comprises triethylamine, in an amount ranging from 0.05 to 0.8 mole per available NH2 group.

18. The process as defined by claim 15, wherein the catalyst comprises a nickel compound which is soluble in liquid phase of the reaction mixture, in an amount ranging from $0.5\times10^{-3}$ to $5\times10^{-3}$ moles per available NH2 group.

* * * * *